US012611317B1

(12) United States Patent
Gililland

(10) Patent No.: US 12,611,317 B1
(45) Date of Patent: Apr. 28, 2026

(54) SYSTEM AND METHOD FOR DETERMINING PELVIC TILT BASED ON ANTERO-POSTERIOR RADIOGRAPHIC IMAGES FOR INTRAOPERATIVE ALIGNMENT OF AN ACETABULAR COMPONENT

(71) Applicant: Orthogrid Systems Holdings, LLC, Midvale, UT (US)

(72) Inventor: Jeremy M. Gililland, Salt Lake City, UT (US)

(73) Assignee: Orthogrid Systems, Inc., Milcreek, UT (US)

( * ) Notice: Subject to any disclaimer, the term of this patent is extended or adjusted under 35 U.S.C. 154(b) by 168 days.

(21) Appl. No.: 18/244,504

(22) Filed: Sep. 11, 2023

Related U.S. Application Data

(60) Provisional application No. 63/405,638, filed on Sep. 12, 2022.

(51) Int. Cl.
*A61F 2/46* (2006.01)
*G06T 7/73* (2017.01)

(52) U.S. Cl.
CPC .......... *A61F 2/4609* (2013.01); *A61F 2/4657* (2013.01); *G06T 7/73* (2017.01); *A61F 2002/4632* (2013.01); *A61F 2002/4668* (2013.01); *G06T 2207/10116* (2013.01); *G06T 2207/30008* (2013.01)

(58) Field of Classification Search
CPC ................................................. A61F 2/4657
See application file for complete search history.

(56) References Cited

U.S. PATENT DOCUMENTS

| | | | |
|---|---|---|---|
| 9,248,002 B2 | 2/2016 | McCarthy | |
| 2014/0276872 A1* | 9/2014 | Song | A61F 2/30942 |
| | | | 606/91 |
| 2015/0088146 A1* | 3/2015 | McCarthy | A61B 17/1666 |
| | | | 606/91 |

OTHER PUBLICATIONS

Atilla, Rear Drop: A New Radiographic Landmark for Estimation of Pelvic Tilt on a Pelvic Radiograph. J of Hip Preserv. Sueg vol. 8, No. 1 pp. 58-66 (May 5, 2021).
Blondel, B. et al. , Sacro-femoral-pubic angle: a coronal Paramter to Estimate Pelvic Tilit, Eur. Sprine J. 12:719-24 ( 2021).
Eckmann, BS et al, Accuracy of Pelvic Flexion Measurements from Lateral Radiographs Clin. Orthop. and Related Res. v, 451 154-60 ( 2006).
Muir, J. etal.A novel Method for Correcting Pelvic Tilt on Anteroposterior Pelvic Radiographs, DOI: 10/7759/cureus.6274 (2019).
Tannast, M. et al, Estimation of Pelvic Tilt on Anteroposterior X-rays—a Comparison of Six Parameters, Skel. Rad. 35:149-155 (2006).

* cited by examiner

*Primary Examiner* — Andrew Yang
(74) *Attorney, Agent, or Firm* — SCHWEGMAN LUNDBERG & WOESSNER, P.A.

(57) ABSTRACT

Functional patient-specific acetabular component alignment is important in total hip arthroplasty. A method for acetabular component alignment by calculating pelvic tilt from an anteroposterior radiograph of the pelvis of a patient may be replicated intraoperatively for patient-specific alignment. A system for automated generation of the pelvic tilt from an anteroposterior radiograph presented improves the efficacy and accuracy of total hip arthroplasty.

9 Claims, 5 Drawing Sheets

System 4

SYSTEM AND METHOD FOR DETERMINING PELVIC TILT BASED ON ANTERO-POSTERIOR RADIOGRAPHIC IMAGES FOR INTRAOPERATIVE ALIGNMENT OF AN ACETABULAR COMPONENT

BACKGROUND OF THE INVENTION

Field of Invention: The subject matter disclosed herein provides a method and system for acetabular component alignment and/or positioning.

Description of the Related Art including information disclosed under 37 CFR 1.97 and CFR 1.98: Instability is one of the most common complications following total hip arthroplasty. Instability is found in approximately 2% of total hip arthroplasty cases and is the most common cause of revision in total hip arthroplasty. Acetabular component malposition is the most common cause of instability in total hip arthroplasty, and it has been suggested that 51% of revision total hip arthroplasty were avoidable, with nearly 50% of those avoidable revisions being due to suboptimal acetabular component positioning. It has been suggested that tradition Lewinnick safe zones fail to properly position the acetabular component by failing to account for functional pelvic tilt in abnormal native anatomy and/or spinopelvic immobility. A patient-specific evaluation of functional pelvic tilt is required for optimal acetabular orientation. Currently employed strategies for determination of pelvic tilt prior to acetabular component positing have involved standing and seated lateral pelvic radiographs to evaluate the functional pelvic plane and to evaluate spinal mobility by the change in sacral slope from sitting to standing. Others have used sitting and standing lateral radiographs to calculate pelvic tilt but not accessed for efficacy in surgery. One method has used standing lateral radiographs to determine pelvic tilt by measuring the angle between the anterosuperior iliac spine and a vertical line from the superior margin of the pubic symphysis. Although these and possibly other previous works have demonstrated the importance of using lateral pelvic radiographs to evaluate pelvic tilt preoperatively, standing anteroposterior pelvic radiographs are more commonly available and can be more easily replicated intraoperatively. Thus an accurate measure of pelvic tilt from an anteroposterior pelvic radiograph can provide a surgical feasible means of determining acetabular component alignment.

An attempt to calculate pelvic tilt from anteroposterior radiographs via the pubic symphysis to sacrococcygeal junction distance (PSCD) has been described, however the sacrococcygeal junction can be difficult to visualize on radiographs and a low correlation coefficient was found in linear regression analysis of patients. Tannast M et al., Skeletal Radiol. 2006; 35(3): 149-155. Atilla describes a method to calculate pelvic tilt from anteroposterior radiographs by a radiographic landmark ("rear drop") to estimate pelvic tilt, however a strong correlation between the method and the symphysis to sacrococcygeal joint method of Tannast was also shown. Atilla H A et al., J Hip Preserv Surg. 2021; 8(1): 58-66. The strong correlation with the method of Tannast suggests the method is similarly ineffective in the surgical setting.

A proper evaluation and understanding of a patient's pelvic tilt is important for several reasons. First, it allows for categorization of patient's preoperative pelvic position when standing; a retroverted pelvis is especially important to note as this has implications for potential anterior instability in the standing position. Second, it allows for proper evaluation of acetabular component positioning, both intraoperative and postoperative, as version and inclination change with pelvic tilt. For instance, an acetabular component that is in 20° of anteversion and 40° of inclination, which are traditional safe zones, in a radiograph of a highly retroverted pelvis would be significantly retroverted and adducted relative to that pelvic position. Third, it is important to be able to recreate the standing pelvic tilt intraoperatively, thus accounting for differences between preoperative and intraoperative radiographs.

McCarty U.S. Pat. No. 9,248,002 discloses a method for aligning an acetabular cup by taking pre-operative lateral and anterior or posterior radiographs. The method sets forth identifying at least three points on the anterior or posterior radiograph and two points on the lateral radiograph, then identifying similar points in an intra-operative image. The method basis its alignment on desired abduction and anteversion angles. Requiring identifying multiple reference points on two differently angled radiographs may increase chance for error, thereby reducing accuracy in alignment. Similarly, using two calculations to judge alignment may increase chance for error, reducing accuracy in the procedure.

A method to determine and perform an acetabular alignment from a single factor, such as pelvic tilt, and using only one radiographic image would be an ideal method for alignment of an acetabular component. In order to avoid acetabular component malposition, a novel, easily reproducible, accurate, and surgical feasible method and system are presented to align an acetabular component from a single anteroposterior radiograph based on a computation of the patient's pelvic tilt.

SUMMARY OF THE INVENTION

The inventive subject matter includes an imaging system and computing platform coupled to the imaging system configured to: obtain at least one anteroposterior image of a patient; generate measurements from the at least one image to provide a calculation of pelvic tilt; and project the calculated pelvic tilt on to the at least one image.

The inventive subject matter also includes a system for aligning an acetabular component during surgery using a computing platform including a processor and an automated computer software, wherein the automated computer software is configured to: receive patient image data, wherein the patient image data is processed by an automated computer software by the processor; wherein the patient image data comprises an anteroposterior radiographic image; locate a trans-teardrop line and a trans-teardrop to pubic symphysis line; determine the distance of the trans-teardrop to pubic symphysis line and the distance of the trans-teardrop line by the automated computer software; calculate by the automated computer software a ratio of the trans-teardrop to pubic symphysis line to the trans-teardrop line using the length of the trans-teardrop to pubic symphysis line over the trans-teardrop line; calculate by the automated computer software a pelvic tilt, wherein the pelvic tilt is derived from the ratio of the trans-teardrop to pubic symphysis line to the trans-teardrop line; output the calculation of pelvic tilt; and the system further comprises the steps of: dynamically displaying the image data and the calculation of pelvic tilt on a graphical user interface.

Another inventive aspect is a method to provide intraoperative surgical guidance to position an acetabular component the method includes the steps of: receiving an anterior posterior pre-operative radiograph of a subject; determining a pelvic tilt from the anterior posterior pre-operative radiograph of a subject, wherein the pelvic tilt is calculated by the steps of: locating a trans-teardrop line from the anterior posterior pre-operative radiograph of the subject, the trans-teardrop line defined by a first point on the most inferior part of the right teardrop and a second point on the most inferior part of the left teardrop; locating the superior portion of the pubic symphysis from the anterior posterior pre-operative radiograph of a subject; determining a trans-teardrop to pubic symphysis line from a measurement of the trans-teardrop line to the superior portion of the pubic symphysis from anterior posterior pre-operative radiograph of a subject; calculating a ratio of the trans-teardrop to pubic symphysis line to the trans-teardrop line using the length of the trans-teardrop to pubic symphysis line over the trans-teardrop line; calculating the pelvic tilt, wherein the pelvic tilt is derived from the ratio of the trans-teardrop to pubic symphysis line to the trans-teardrop line; receiving an intra-operative image of the subject; and intraoperatively positioning the acetabular component based on the pelvic tilt of the subject in need of acetabular component positioning.

BRIEF DESCRIPTION OF THE DRAWINGS

The novel features of the invention are set forth with particularity in the claims. Features and advantages of the present invention are referred to in the following detailed description, and the accompanying drawings of which:

DETAILED DESCRIPTION OF THE INVENTION

Figure 1:
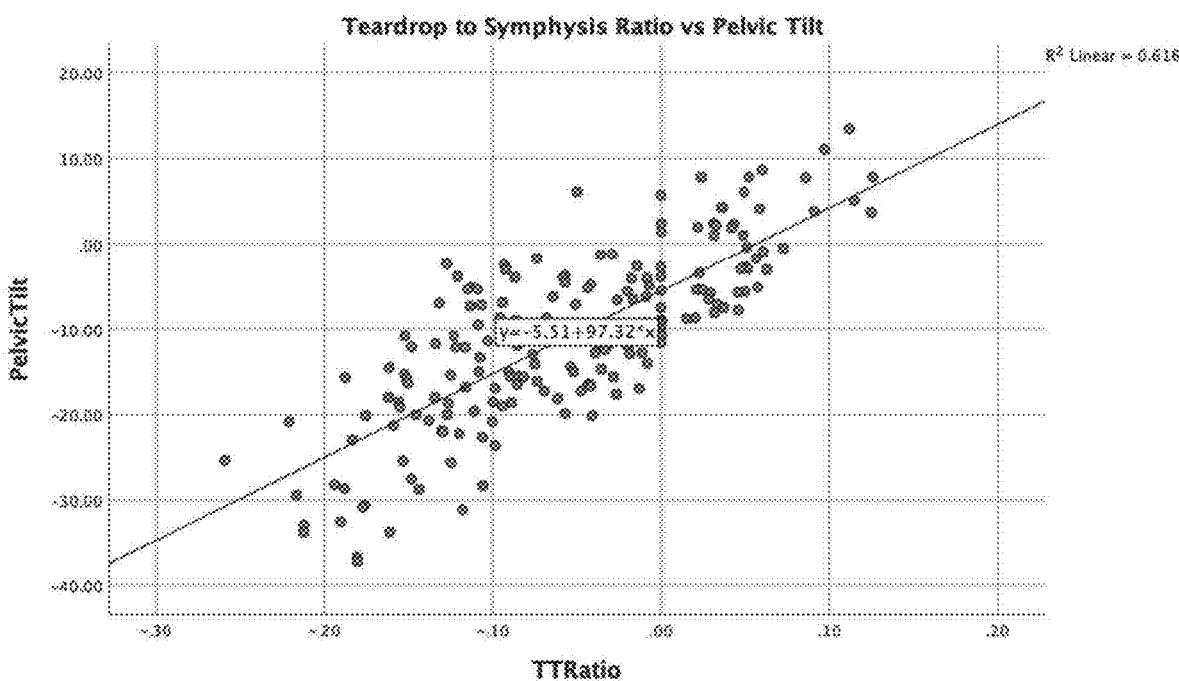
FIG. 1 shows a linear regression analysis of the ratio of the length of trans-teardrop to pubic symphysis line (TTPS) over the length of the trans-teardrop line (TT), labeled as (TTPS/TT) and pelvic tilt (PT) for male and female patients.

The details of one or more embodiments of the presently disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Unless defined otherwise, all technical and scientific terms used herein have the same meaning as commonly understood by one of ordinary skill in the art to which the presently disclosed subject matter belongs. Although any methods, devices, and materials similar or equivalent to those described herein can be used in the practice or testing of the presently disclosed subject matter, representative methods, devices, and materials are now described. Following long-standing patent law convention, the terms "a", "an", and "the" refer to "one or more" when used in this application, including the claims. Thus, for example, reference to "a cell" includes a plurality of such cells, and so forth. All references to singular characteristics or limitations of the present disclosure shall include the corresponding plural characteristic(s) or limitation(s) and vice versa, unless otherwise specified or clearly implied to the contrary by the context in which the reference is made. All combinations of method or process steps as used herein can be performed in any order, unless otherwise specified or clearly implied to the contrary by the context in which the referenced combination is made. The methods and compositions of the present disclosure, including components thereof, can comprise, consist of, or consist essentially of the essential elements and limitations of the embodiments described herein, as well as any additional or optional components or limitations described herein or otherwise useful. Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method. As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed.

The presently disclosed subject matter provides a system and method to provide intraoperative surgical guidance, and assist with positioning of the acetabular component of a total hip arthroplasty based on pelvic tilt derived from standing radiographs of the subject in a way that is easily reproducible and has a high correlation coefficient in linear regression analysis.

Using an imaging system and a computing platform, at least one digital measuring tool is overlayed on the intra-operative images and these tools assist the surgeon with adjusting the acetabular component position specific to that patient's anatomy and their functional pelvic tilt based on a pre-operative standing antero-posterior pelvis radiographic image. The novel methods described in the description of the invention assist with intra-operative recreation of pre-operative pelvic tilt and thus help the surgeon with patient specific functional placement of the acetabular component of a total hip arthroplasty.

This method uses the trans-teardrop line to superior pubic symphysis distance as a surrogate for pelvic tilt (defined as a measurement obtained from lateral radiographs by measuring the angle between a vertical line and a line from the anterosuperior illac spine to the center of superior margin of the pubic symphysis) and can be used in any clinical and surgical setting, requiring only a standing anteroposterior pelvis radiographic image. An equation for calculating pelvic tilt (PT) 2 from anteroposterior radiographs was derived. First pelvic tilt was calculated from lateral radiographs, defined as pelvic tilt$(PT)_1$. Lateral radiographs and corresponding standing anteroposterior radiographs were collected from two hundred human patients' pre-surgery.

Pelvic tilt was first calculated from the lateral radiographs by measuring the angles between both left and right anterosuperior iliac spine $(ASIS_{left, \, right})$ and a vertical line from the center of superior margin of the pubic symphysis (PS) as previously described by Eckman K et al., Clin Orthop Relat Res. 2006; 451:154-160. Landmarks were set as the following points: $ASIS_{left}$, $ASIS_{right}$, and pubic symphysis (PS). A vertical line may be drawn from the pubic symphysis (PS) with respect to the side of the page of the radiograph image up to a height corresponding to the point of an anterosuperior iliac spine (ASIS).

Lines may be drawn from the $ASIS_{left, right}$ to the pubic symphysis (PS). The angle between both lines from pubic symphysis (PS) to $ASIS_{left, right}$ may be averaged to calculate pelvic tilt. The calculation may be represented by the following equations:

$$(PT)_{left} = \text{Cos}(a) = D_{1left}/D_2 \qquad \text{<Equation 1>}$$

$$(PT)_{right} = \text{Cos}(a) = D_{1right}/D_2 \qquad \text{<Equation 2>}$$

$$(PT)_1 = (PT)_{left} + (PT)_{right}/2 \qquad \text{<Equation 3>}$$

Where $D_{1 left, right}$ is the distance from the $ASIS_{left, right}$, respectively, to pubic symphysis (PS); $D_2$ is the distance of the vertical line; and pelvic tilt $(PT)_1$ is pelvic tilt calculated from lateral radiographic image. Overall, the average pelvic tilt of all patients was $-10.7°$ (SD=9.8°); only 25 patients had anterior pelvic tilt. In sub analysis by gender, the average pelvic tilt was $-9.7°$ (SD=10.1) in females and $-12.3°$ (SD=9.0) in males. The average distance from the trans-teardrop line to the top of the pubic symphysis line (TTPS) was $-6.3$ mm (SD=9.7 mm). In the patients with a pubic symphysis TTPS of approximately 0 mm, the average pelvic tilt was $-6.0°$ (SD=5.5'). In those patients with a pelvic tilt within 3° of neutral (25 patients), the average TTPS was 1.5 mm (SD=6.9 mm). The corresponding standing anteroposterior radiographs were used to determine a ratio of the length of trans-teardrop to pubic symphysis line (TTPS) over the length of the trans-teardrop line (TT), labeled as (TTPS/TT). PS is the top of the pubic symphysis, TTPS is the distance from the Trans Teardrop Line to the top of the Pubic Symphysis (PS).

The trans-teardrop line (TT) is the point from most inferior point on the teardrops of each side of the pelvis. The trans-teardrop to pubic symphysis line is the vertical distance between the trans-teardrop line and the superior margin of the pubic symphysis (TTPS). The teardrop and pubic symphysis are more easily recognizable and thus allow for more accurate measurements from pelvic radiographs. Additionally, anteroposterior radiographs are regularly performed by physicians prior to acetabular component positioning. For these reasons, the method is superior in providing a surgically feasible way to begin acetabular component alignment. The calculation can be represented by the following equation:

$$(TTPS/TT) = (TTPS)/(TT) \qquad \text{<Equation 4>}$$

Now referring to FIG. 1, Linear regression analysis of ratio of the length of trans-teardrop to pubic symphysis line (TTPS) over the length of the trans-teardrop line (TT), TTPS/TT calculated from anteroposterior pelvic radiograph and pelvic tilt $(PT)_1$ calculated from lateral pelvic radiograph. Linear regression analysis was then performed on the cohort as a whole and a sub-analysis was performed on separated male and female cohorts. R and R2 values were calculated, and a linear equation was made using the regression analysis. The average TTPS/TT ratio was $-0.054$ (SD=0.079; range: $-0.26$ to 0.13). There was a strong correlation between the TTPS/TT on the anteroposterior radiographs and the pelvic tilt on the lateral radiographs (r=0.785, r2=0.616, p<0.001).

The linear equation may be represented as:

$$(PT)_2 = [97.32(TTPS/TT)] - 5.51 \qquad \text{<Equation 5>}$$

Figure 2:
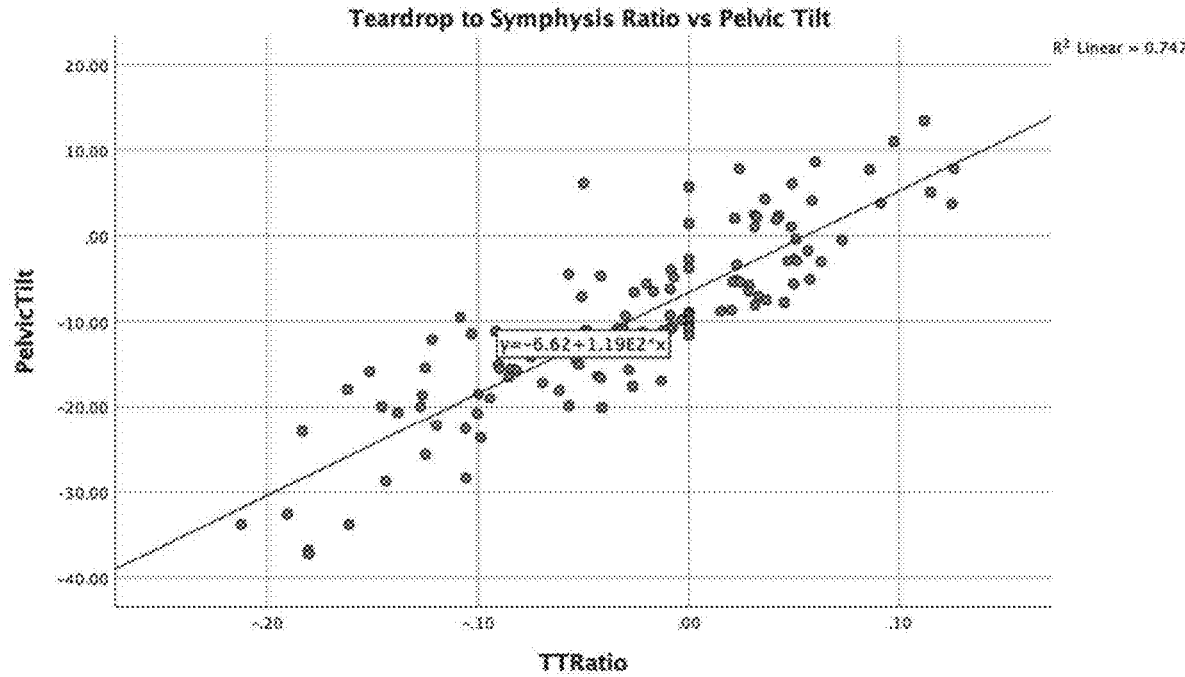
FIG. 2 shows a linear regression analysis of the ratio of the length of trans-teardrop to pubic symphysis line (TTPS) over the length of the trans-teardrop line (TT), labeled as (TTPS/TT) and pelvic tilt (PT) for female patients.

Now referring to FIG. 2, Statistical analysis of FIG. 1 for female cohorts alone. Linear regression analysis was then performed on the cohort. R and R2 values were calculated, and a linear equation was made using the regression analysis. For sub analysis of only female patients, this correlation was even stronger (r=0.864, r2=0.747, p<0.001). The linear equation may be represented as:

$$(PT)_{2, female} = [98.43(TTPS/TT)] - 2.8 \qquad \text{<Equation 6>}$$

Figure 3:
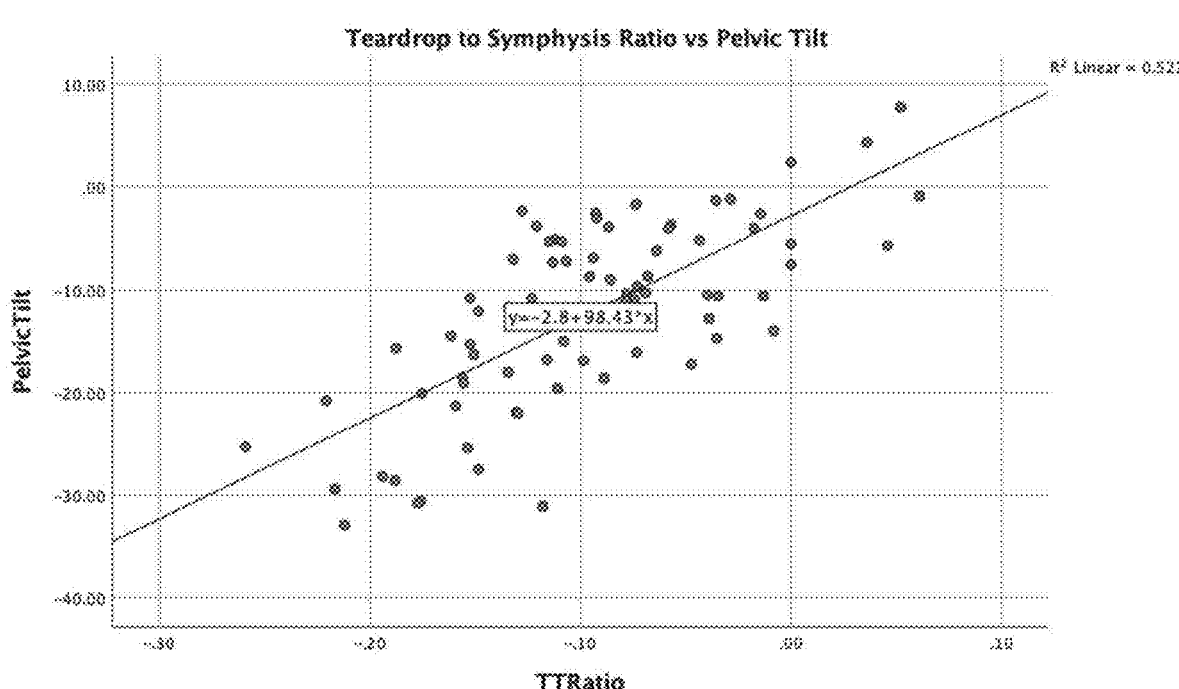
FIG. 3 shows a linear regression analysis of the ratio of the length of trans-teardrop to pubic symphysis line (TTPS) over the length of the trans-teardrop line (TT), labeled as (TTPS/TT) and pelvic tilt (PT) for male patients.

Now referring to FIG. 3, Statistical analysis of FIG. 1 for male cohorts alone. Linear regression analysis was then performed on the cohort. R and R2 values were calculated, and a linear equation was made using the regression analysis. Sub analysis of male patients also demonstrated a significant correlation (r=0.723, r2=0.522, p<0.001). The linear equation may be represented as:

$$(PT)_{2, male} = [119.0(TTPS/TT)] - 6.62 \qquad \text{<Equation 7>}$$

Figure 4:
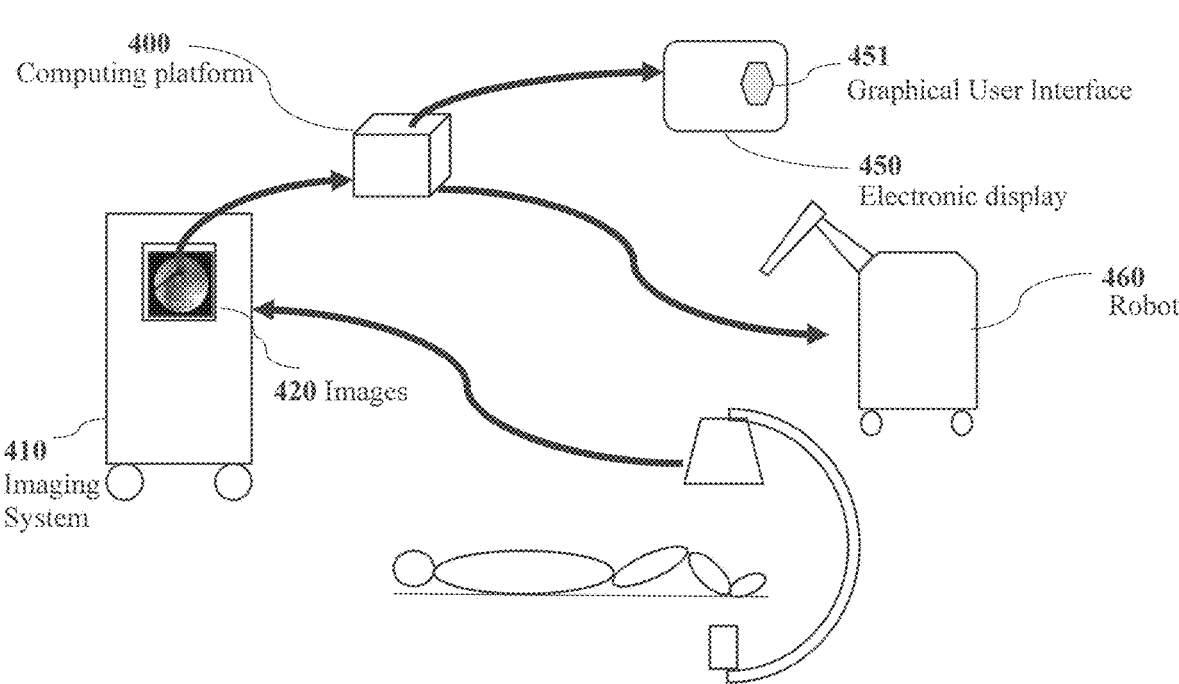
FIG. 4 shows a system including an imaging system and computing platform for carrying out the method of the present invention.

Now referring to FIG. 4, imaging system 410 and a processor for automated processing of data may be used in a system 4 for the performance of the present method. FIG. 4 is a diagram illustrating an exemplary system using having a computing platform 400 with a processor for an automated computing software that may perform at least: calculations including the equations included herein; providing a graphical user interface 451 on an electronic display 450; digital image analysis; and other computer processes such as running an artificial intelligence engine or directing a surgical robot 460 according to the methods of the subject matter described herein. The imaging system includes: Image Intensified Fluoroscopic Imaging Systems, Digital Fluoroscopic Imaging Systems, and Digital Radiographic Imaging Systems.

The computing platform 400 includes at least one processor and memory. The subject matter described herein can be implemented in automated computer software in combination with hardware and/or firmware. For example, the subject matter described herein can be implemented in software executed by at least one processor. In one exemplary implementation, the subject matter described herein can be implemented using a computer readable medium having stored thereon computer executable instructions that when executed by the processor of a computer control the computer to perform steps. Exemplary computer readable media suitable for implementing the subject matter described herein include non-transitory devices, such as disk memory devices, chip memory devices, programmable logic devices, and application specific integrated circuits. In addition, a computer readable medium that implements the subject matter described herein can be located on a single device or computing platform or can be distributed across multiple devices or computing platforms. As used herein, the terms "function" or "module" refer to hardware, firmware, or software in combination with hardware and/or firmware for implementing features described herein.

An imaging system 410 obtains images 420, such as pre-operative radiographic images or intraoperative fluoroscopic of a patient's anatomy. Exemplary radiographic images can be captured, for example, by a portable fluoroscopy machine called a C-arm. In some embodiments, the computing platform 400 and/or a related module can be configured to perform one or more aspects associated with automated intra-operative imaging. For example, the computing platform 400 and/or a related module can receive an inter-operative surgical image, e.g., a fluoroscopic image of the pelvis.

All display or visualization of images 451 and information can be displayed and rendered using electronic display 450, augmented reality, mixed devices as a graphical user interface 451. The electronic display 450 may be an electronic display device, such as a computer monitor, a heads-up display, such as Glass (Google), or other electronic visualization medium. The automated computing software may be provided overlay pre-operative or intra operative images and dimensioned grids on an electronic display 450. Data captured may be stored in data storage in the memory of the computing platform 400 or externally.

The system 4 includes: an input of a series of radiographic or fluoroscopic images of a selected surgical site, a computing platform 400 to process the surgical images and overlay a virtual, augmented, or holographic dimensioned grid on surgical images, with an input device, such as a mouse, to provide selection of points corresponding to anatomical landmarks, e.g. ASIS or (PS), and generation or manipulation of dimensioned grids. The computing platform 400 including automated computing software may provide for digital image analysis. The digital image analysis may be trained and/or programed for automatic recognition of anatomical landmarks.

The computing platform 400 may perform other computing task such as running an artificial intelligent engine or directing a surgical robot 460. A surgical robot 460 has the capability to take images 420 to the preference of a surgeon and/or assist in another surgical task. An artificial intelligence engine, utilizes and analyzes the information from datasets to provide output information useful in the surgical process, e.g. recognition of anatomical landmarks or predicting, based on calculated pelvic tilt, a potential acetabular component positioning may result in malposition of the component.

To predict potential malposition of a component the artificial intelligence engine can be trained for recognition of malposition by a surgeon or from datasets of known acetabular component alignment. The artificial intelligence engine may consider the calculated $(PT)_2$ of the patient recognizing potential malposition and guide by the computing platform 400 a surgeon to a correct alignment. Information datasets analyzed include procedural medical image datasets, such as intraoperative fluoroscopic images, pre- and post-operative radiograph, or other post-operative imaging. The datasets may also include collected reference data of prior hip arthroplasties based on computed tomography data or other datasets, such as: peer-reviewed literature and clinical studies datasets; known predictors and indicators of complications datasets; 3D statistical models of human anatomy datasets; other medical image datasets.

In order to automatically recognize anatomical landmarks in a radiographic image the artificial intelligence engine can be trained for recognition, for example of the ASIS and PS, by neural network learning or other artificial intelligence methods. A user may assist the artificial intelligence engine in the build-up of an anatomical landmark recognition program by confirming or denying automated recognition datasets from radiographic images. The artificial intelligence engine may also utilize other learned models for anatomical feature tracking as an input dataset.

Figure 5:
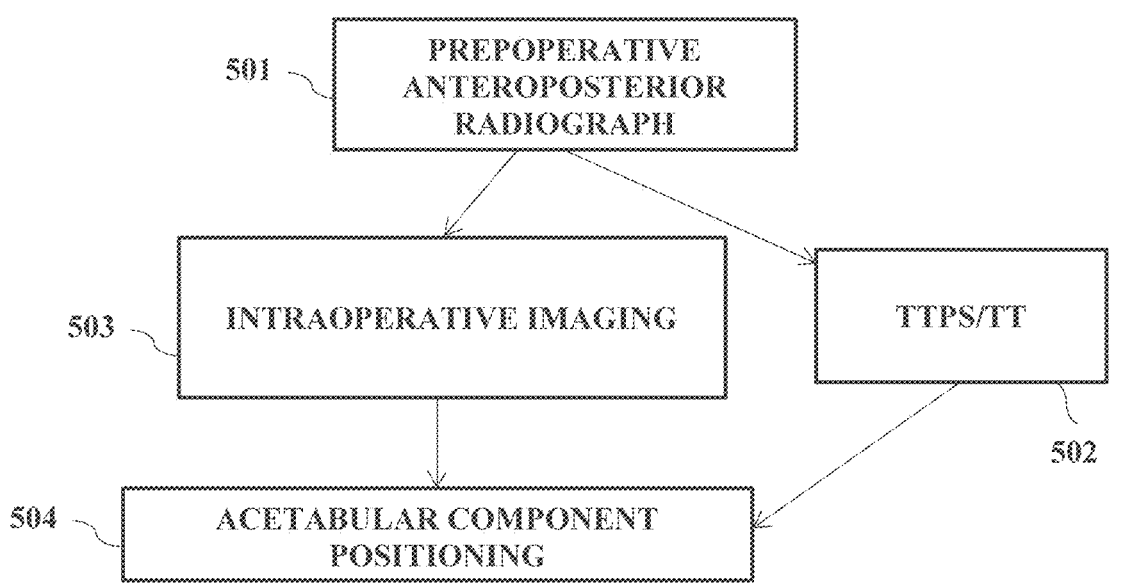
FIG. 5 provides a method for intraoperative positioning an acetabular component during arthroplasty.

Now referring to FIG. 5, a method for performing acetabular component positioning is shown. A pre-operative anteroposterior radiographic image 501 may be received from a patient by a user or machine, such as the computing platform 400 and imaging system 410 of FIG. 4. Anatomical landmarks and TTPS/TT 502 may be calculated by user or machine, such as the computing platform 400 and imaging system 410 of FIG. 4. Intra-operative imaging 503 capturing an area for acetabular component alignment may be received by a user or machine, such as the computing platform 400 and imaging system 410 of FIG. 4. Acetabular component positioning 504 is then performed through a determination of pelvic tilt, (PT) z, calculated from the TTPS/TT 502 of the anteroposterior radiographic image. Intra-operative imaging 503 may capture a potential alignment of the acetabular component and may guide a performer of the present method in acetabular component positioning 504.

While the invention has been described with reference to details of the illustrated embodiments, these details are not intended to limit the scope of the invention as defined in the appended claims. The embodiment of the invention in which exclusive property or privilege is claimed is defined as follows:

Each example is provided by way of explanation of the present disclosure and is not a limitation thereon. In fact, it will be apparent to those skilled in the art that various modifications and variations can be made to the teachings of the present disclosure without departing from the scope of the disclosure. For instance, features illustrated or described as part of one embodiment can be used with another embodiment to yield a still further embodiment. While the terms used herein are believed to be well understood by one of ordinary skill in the art, definitions are set forth herein to facilitate explanation of the presently disclosed subject matter.

What is claimed is:

1. A method to provide intraoperative surgical guidance to position an acetabular component comprising:

receiving an anterior posterior pre-operative radiograph of a subject;

determining a pelvic tilt from the anterior posterior pre-operative radiograph of a subject, wherein the pelvic tilt is calculated by the steps of:

locating a trans-teardrop line from the anterior posterior pre-operative radiograph of the subject, the trans-teardrop line defined by a first point on the most inferior part of the right teardrop and a second point on the most inferior part of the left teardrop;

locating the superior portion of the pubic symphysis from the anterior posterior pre-operative radiograph of a subject;

determining a trans-teardrop to pubic symphysis line from a measurement of the trans-teardrop line to the superior portion of the pubic symphysis from anterior posterior pre-operative radiograph of a subject;

calculating a ratio of the trans-teardrop to pubic symphysis line to the trans-teardrop line using the length of the trans-teardrop to pubic symphysis line over the trans-teardrop line;

calculating the pelvic tilt, wherein the pelvic tilt is derived from the ratio of the trans-teardrop to pubic symphysis line to the trans-teardrop line;

receiving an intraoperative image of the subject; and intraoperatively positioning the acetabular component based on the pelvic tilt of the subject in need of acetabular component positioning.

2. The method of claim 1, wherein the step of intra-operatively positioning the acetabular component comprises overlaying the intraoperative image with an at least one digital measuring tool.

3. A system comprising: an imaging system and computing platform coupled to the imaging system configured to:

obtain at least one anteroposterior image of a patient;

generate measurements from the at least one anteroposterior image to provide a calculation of pelvic tilt, wherein the calculation of pelvic tilt comprises;

locating a trans-teardrop line defined by a first point on a most inferior part of a right teardrop and a second point on the most inferior part of a left teardrop from the at least one anteroposterior image;

locating a superior portion of a pubic symphysis from the at least one anteroposterior image;

determining a trans-teardrop to pubic symphysis line from a measurement of the trans-teardrop line to the superior portion of the pubic symphysis;

calculating a ratio of the trans-teardrop to pubic symphysis line to the trans-teardrop line using a length of the trans-teardrop to pubic symphysis line over the trans-teardrop line; and deriving the pelvic tilt from the ratio of the trans-teardrop to pubic symphysis line to the trans-teardrop line; and project calculated pelvic tilt on to at least one intraoperative image anteroposterior image of the patient for intraoperatively positioning an acetabular component.

4. A system for providing surgical guidance with a computing platform comprising:

a processor and an automated computer software, wherein the automated computer software is configured to:

receive a patient image data of a subject, wherein the patient image data is processed by an automated computer software by the processor, wherein the patient image data comprises at least an anteroposterior radiographic image;

locate a trans-teardrop line and a trans-teardrop to a pubic symphysis line;

determine the distance of the trans-teardrop to the pubic symphysis line and the distance of the trans-teardrop line by the automated computer software;

calculate by the automated computer software a ratio of the trans-teardrop to pubic symphysis line to the trans-teardrop line using the length of the trans-teardrop to pubic symphysis line over the trans-teardrop line;

calculate by the automated computer software a pelvic tilt, wherein the pelvic tilt is derived from the ratio of the trans-teardrop to pubic symphysis line to the trans-teardrop line; and output the calculation of the pelvic tilt;

receive an intraoperative image of the subject; and overlay the image data and the calculation of the pelvic tilt on a graphical user interface to provide surgical guidance for intraoperatively positioning an acetabular component based on the pelvic tilt of the subject in need of acetabular component positioning.

5. The system of claim 4, the automated computer software further configured to:

receive at least one intra-operative image of the pelvis of the patient, wherein the intra-operative image captures an alignment of an acetabular component; and intra-operatively align the acetabular component from the alignment of the acetabular component from the at least one intra-operative image.

6. The system of claim 4, the automated computer software further configured to map a grid to the patient image data to provide a processed image data.

7. The system of claim 4, wherein locating the trans-teardrop line and the trans-teardrop to pubic symphysis line further comprises:

providing by the automated computer software a graphical user interface for selecting a left and right most inferior part of the teardrop from the patient image data;

selecting a superior portion of the pubic symphysis the within the patient image data;

and generating by the automated computer software the trans-teardrop to pubic symphysis line and the trans-teardrop line.

8. The system of claim 4, wherein locating the trans-teardrop line and the trans-teardrop to pubic symphysis line further comprises:

accessing the patient image data by a digital image analysis software, wherein the digital image analysis software locates the left and right most inferior part of the teardrop from the patient image data and wherein the digital image analysis software locates a superior portion of the pubic symphysis from the patient image data; and generating by the automated computer software the trans-teardrop to pubic symphysis line and the trans-teardrop line.

9. The system of claim 4, the automated computer software further configured to:

provide an artificial intelligence engine and at least one dataset configured to output information, wherein the dataset at least comprises the patient image data and a reference set;

generate by the artificial intelligence engine the output information based on the dataset; and dynamically display output information on a graphical user interface.

* * * * *